United States Patent
Lennox

(10) Patent No.: US 8,262,613 B2
(45) Date of Patent: *Sep. 11, 2012

(54) LOCALIZED DELIVERY OF DRUG AGENTS

(75) Inventor: Charles D. Lennox, Hudson, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,131

(22) Filed: Jun. 21, 2011

(65) Prior Publication Data

US 2011/0251582 A1  Oct. 13, 2011

Related U.S. Application Data

(63) Continuation of application No. 11/107,730, filed on Apr. 18, 2005, which is a continuation of application No. 09/891,420, filed on Jun. 27, 2001, now Pat. No. 6,939,320, which is a continuation of application No. 09/080,237, filed on May 18, 1998, now Pat. No. 6,280,411.

(51) Int. Cl.
 *A61M 29/00* (2006.01)
(52) U.S. Cl. ............... 604/103.02; 604/103.11; 604/919
(58) Field of Classification Search .................... 604/96, 604/101, 265, 103–104, 500, 507–509, 96.01, 604/101.01, 101.02, 103.01, 103.02, 103.05, 604/103.06, 103.11, 103.12, 915, 917, 103.09; 606/108, 192, 194, 198; 623/1.1, 1.11, 1.15, 623/1.18, 1.2, 1.23, 1.39, 1.4, 1.42, 1.43, 623/1.44, 1.45, 1.46
See application file for complete search history.

(56) References Cited

U.S. PATENT DOCUMENTS

| 4,417,576 A | 11/1983 | Baran |
| 4,423,725 A | 1/1984 | Baran et al. |
| 4,994,033 A | 2/1991 | Shockey et al. |

(Continued)

FOREIGN PATENT DOCUMENTS

DE  20321514 U1  10/2007

(Continued)

OTHER PUBLICATIONS

Kito, H., et al., "A Total Delivery System of Genetically Engineered Drugs or Cells for Diseased Vessels—Concept, Materials, and Fabricated Prototype Device," ASAIO Journal 1994, vol. 40, No. 3, M260-M266.

(Continued)

*Primary Examiner* — Quynh-Nhu H Vu
(74) *Attorney, Agent, or Firm* — Kenyon & Kenyon LLP

(57) ABSTRACT

Medical devices including a substrate that are expandable from a compressed state to an expanded state; a coating on the substrate, the coating having a drug agent incorporated therein; and a sheath over the coating. The sheath is expandable from a compressed state to an expanded state and has at least one perforation therein. The medical devices are configured such that when the substrate is in a compressed state, the sheath is also in a compressed state and the perforation is substantially closed. When the substrate is in an expanded state, the sheath is also in an expanded state and the perforation is substantially open. The invention also includes a method of using the medical devices for the controlled, localized delivery of a drug agent to a target location within a mammalian body.

20 Claims, 3 Drawing Sheets

U.S. PATENT DOCUMENTS

| | | | |
|---|---|---|---|
| 4,994,072 A | 2/1991 | Bhate et al. | |
| 5,015,231 A | 5/1991 | Keith et al. | |
| 5,042,976 A | 8/1991 | Ishitsu et al. | |
| 5,049,132 A | 9/1991 | Shaffer et al. | |
| 5,091,205 A | 2/1992 | Fan | |
| 5,092,841 A | 3/1992 | Spears | |
| 5,100,386 A | 3/1992 | Inoue | |
| 5,102,402 A | 4/1992 | Dror et al. | |
| 5,141,494 A | 8/1992 | Danforth et al. | |
| 5,195,969 A | 3/1993 | Wang et al. | |
| 5,196,024 A | 3/1993 | Barath | |
| 5,213,576 A | 5/1993 | Abiuso et al. | |
| 5,226,913 A | 7/1993 | Pinchuk | |
| 5,232,444 A | 8/1993 | Just et al. | |
| 5,292,321 A | 3/1994 | Lee | |
| 5,295,959 A | 3/1994 | Gurbel et al. | |
| 5,304,121 A | 4/1994 | Sahatjian | |
| 5,320,604 A | 6/1994 | Walker et al. | |
| 5,324,261 A | 6/1994 | Amundson et al. | |
| 5,348,538 A | 9/1994 | Wang et al. | |
| 5,352,236 A | 10/1994 | Jung et al. | |
| 5,364,356 A | 11/1994 | Hofling | |
| 5,370,614 A | 12/1994 | Amundson et al. | |
| 5,383,928 A | 1/1995 | Scott et al. | |
| 5,397,307 A | 3/1995 | Goodin | |
| 5,447,497 A * | 9/1995 | Sogard et al. | 604/101.02 |
| 5,456,666 A | 10/1995 | Campbell et al. | |
| 5,464,650 A | 11/1995 | Berg et al. | |
| 5,498,238 A | 3/1996 | Shapland et al. | |
| 5,499,971 A | 3/1996 | Shapland et al. | |
| 5,501,662 A | 3/1996 | Hofmann | |
| 5,505,700 A | 4/1996 | Leone et al. | |
| 5,507,724 A | 4/1996 | Hofmann et al. | |
| 5,545,132 A | 8/1996 | Fagan et al. | |
| 5,545,208 A | 8/1996 | Wolff et al. | |
| 5,562,922 A | 10/1996 | Lambert | |
| 5,571,086 A | 11/1996 | Kaplan et al. | |
| 5,599,306 A | 2/1997 | Klein et al. | |
| 5,624,411 A | 4/1997 | Tuch | |
| 5,626,600 A | 5/1997 | Horzewski et al. | |
| 5,634,901 A | 6/1997 | Alba et al. | |
| 5,653,689 A | 8/1997 | Buelna et al. | |
| 5,674,192 A | 10/1997 | Sahatjian et al. | |
| 5,679,400 A | 10/1997 | Tuch | |
| 5,685,847 A * | 11/1997 | Barry | 604/96.01 |
| 5,693,014 A | 12/1997 | Abele et al. | |
| 5,704,908 A | 1/1998 | Hofmann et al. | |
| 5,707,358 A | 1/1998 | Wright | |
| 5,707,385 A | 1/1998 | Williams | |
| 5,738,901 A | 4/1998 | Wang et al. | |
| 5,746,745 A | 5/1998 | Abele et al. | |
| 5,749,915 A | 5/1998 | Slepian | |
| 5,810,870 A | 9/1998 | Myers et al. | |
| 5,833,651 A | 11/1998 | Donovan et al. | |
| 5,833,659 A | 11/1998 | Kranys | |
| 5,843,089 A | 12/1998 | Sahatjian et al. | |
| 5,893,840 A | 4/1999 | Hull et al. | |
| 5,941,871 A | 8/1999 | Adams et al. | |
| 5,947,925 A | 9/1999 | Ashiya et al. | |
| 5,964,730 A | 10/1999 | Williams et al. | |
| 6,129,706 A | 10/2000 | Janacek | |
| 6,135,982 A | 10/2000 | Campbell | |
| 6,149,641 A | 11/2000 | Ungs | |
| 6,280,411 B1 * | 8/2001 | Lennox | 604/103.05 |
| 6,364,856 B1 | 4/2002 | Ding et al. | |
| 6,369,039 B1 | 4/2002 | Palasis et al. | |
| 6,450,989 B2 | 9/2002 | Dubrul et al. | |
| 6,517,514 B1 | 2/2003 | Campbell | |
| 6,544,221 B1 | 4/2003 | Kokish et al. | |
| 6,544,223 B1 | 4/2003 | Kokish | |
| 6,547,803 B2 | 4/2003 | Seward et al. | |
| 6,593,130 B1 | 7/2003 | Sen et al. | |
| 6,638,246 B1 | 10/2003 | Naimark et al. | |
| 6,652,581 B1 | 11/2003 | Ding | |
| 6,656,155 B2 | 12/2003 | Freyman | |
| 6,656,162 B2 | 12/2003 | Santini, Jr. et al. | |
| 6,743,388 B2 | 6/2004 | Sridharan et al. | |
| 6,765,059 B2 | 7/2004 | Corley | |
| 6,796,958 B2 | 9/2004 | Chen et al. | |
| 6,939,320 B2 * | 9/2005 | Lennox | 604/103.02 |
| 6,991,617 B2 | 1/2006 | Hektner et al. | |
| 7,048,714 B2 | 5/2006 | Richter | |
| 7,081,113 B2 | 7/2006 | Sutton | |
| 7,166,099 B2 | 1/2007 | Devens, Jr. | |
| 7,364,585 B2 | 4/2008 | Weber | |
| 7,572,625 B2 | 8/2009 | Davis et al. | |
| 2004/0049259 A1 | 3/2004 | Strecker | |
| 2004/0127978 A1 | 7/2004 | Sparer et al. | |
| 2004/0181252 A1 | 9/2004 | Boyle et al. | |
| 2004/0215227 A1 | 10/2004 | McMorrow et al. | |
| 2005/0015046 A1 | 1/2005 | Weber et al. | |
| 2005/0182361 A1 * | 8/2005 | Lennox | 604/103.01 |
| 2005/0228417 A1 | 10/2005 | Teitelbaum et al. | |
| 2005/0273049 A1 | 12/2005 | Krulevitch et al. | |
| 2006/0079836 A1 | 4/2006 | Holman et al. | |
| 2006/0167407 A1 | 7/2006 | Weber et al. | |
| 2006/0184112 A1 | 8/2006 | Horn et al. | |
| 2006/0190022 A1 | 8/2006 | Beyar et al. | |
| 2007/0106215 A1 | 5/2007 | Olsen et al. | |
| 2007/0184085 A1 | 8/2007 | Radhakrishnan et al. | |
| 2008/0021385 A1 | 1/2008 | Barry et al. | |
| 2008/0140002 A1 | 6/2008 | Ramzipoor et al. | |
| 2009/0227948 A1 | 9/2009 | Chen et al. | |
| 2009/0227949 A1 | 9/2009 | Knapp et al. | |
| 2011/0054396 A1 | 3/2011 | Kangas et al. | |

FOREIGN PATENT DOCUMENTS

| | | |
|---|---|---|
| EP | 0712615 A1 | 5/1996 |
| EP | 0835673 A2 | 4/1998 |
| EP | 1062966 A1 | 12/2000 |
| EP | 1462127 A1 | 9/2004 |
| EP | 1 595 569 A2 | 11/2005 |
| SU | 1069826 A1 | 1/1984 |
| WO | 9423787 A1 | 10/1994 |
| WO | 9600597 A1 | 1/1996 |
| WO | 9049908 A1 | 10/1999 |
| WO | 03/011363 A2 | 2/2003 |
| WO | 2004060471 A1 | 7/2004 |
| WO | 2005/027996 A2 | 3/2005 |
| WO | 2005037339 A1 | 4/2005 |
| WO | 2005113058 A1 | 12/2005 |
| WO | 2006042260 A2 | 4/2006 |
| WO | 2006138013 A1 | 12/2006 |
| WO | 2007055732 A1 | 5/2007 |
| WO | 2007090385 A2 | 8/2007 |
| WO | 2007117755 A2 | 10/2007 |
| WO | 2008021019 A2 | 2/2008 |
| WO | 2008021025 A1 | 2/2008 |
| WO | 2008086794 A2 | 7/2008 |
| WO | 2009005933 A1 | 1/2009 |
| WO | 2009/046206 A1 | 4/2009 |
| WO | 2009121565 A2 | 10/2009 |

OTHER PUBLICATIONS

European Patent Office, International Search Report and Written Opinion of the International Searching Authority, from related International Application No. PCT/US2009/036359, mailed Jun. 16, 2009.

European Patent Office, International Search Report and Written Opinion of the International Searching Authority in related International application No. PCT/US2009/036354, mailed Jul. 2, 2009.

European Patent Office, partial International Search Report of the International Searching Authority in related International application No. PCT/US2009/036354, mailed May 26, 2009.

Annex to Form PCT/ISA/206—Communication Relating to the Results of the Partial International Search, mailed Dec. 28, 2010, from related International Application No. PCT/US2010/045877.

International Search Report and Written Opinion of the International Searching Authority, mailed Feb. 15, 2011, from related International Application No. PCT/US2010/045877.

* cited by examiner

LOCALIZED DELIVERY OF DRUG AGENTS

CROSS REFERENCE TO RELATED APPLICATION

This application is a continuation of U.S. Ser. No. 11/107,730, filed Apr. 18, 2005, which is a continuation of U.S. Ser. No. 09/891,420, filed Jun. 27, 2001, now U.S. Pat. No. 6,939,320, which is a continuation of U.S. Ser. No. 09/080,237 filed May 18, 1998, now U.S. Pat. No. 6,280,411, all of which are hereby incorporated by reference in its entirety.

FIELD OF THE INVENTION

The present invention relates to methods and devices for the controlled, localized delivery of drug agents within a mammalian body.

BACKGROUND OF THE INVENTION

The systemic administration of drug agents, such as by transoral or intravenous means, treats the body as a whole even though the disease to be treated may be localized. In such a case, systemic administration may not be desirable because the drug agents may have unwanted effects on parts of the body which are not to be treated, or because treatment of the diseased part of the body requires a high concentration of drug agent that may not be achievable by systemic administration.

It is therefore often desirable to administer drug agents at localized sites within the body. Common examples include cases of localized disease (e.g., heart disease) or occluded body lumens. Various methods have been proposed for such localized drug administration. For example, U.S. Pat. No. 5,304,121, which is incorporated herein by reference, discloses a method of delivering water-soluble drugs to tissue at desired locations of a body lumen wall. The method generally includes the steps of impregnating a hydrogel polymer on a balloon catheter with an aqueous drug solution, inserting the catheter into a blood vessel to a desired location, and expanding the catheter balloon against the surrounding tissue to allow the release of the drug.

One of the potential drawbacks to conventional drug delivery techniques using drug-impregnated polymer coatings on balloon catheters is the possible premature diffusion of the drug out of the coating during delivery into the body. Two solutions to this problem have been proposed: the use of a removable sheath over the polymer coating, and the use of a dissolvable or meltable temporary coating over the polymer coating to protect and retain the drug agent in the coating prior to a time of desired administration at a target location. The sheath approach, however, adds considerable profile to the balloon catheter device, making access to small body lumens difficult or impracticable. Furthermore, the use of a temporary protective coating over a drug-impregnated polymer coating may place undesirable time constraints on the drug delivery procedure. Moreover, it is difficult to identify or develop temporary coatings that permit the release of the drug in a consistent and predictable manner.

In view of the potential drawbacks to conventional drug delivery techniques, there exists a need for a device and method for the controlled, localized delivery of drug agents to target locations within a mammalian body while avoiding the premature release of drug agent during delivery.

SUMMARY OF THE INVENTION

In one aspect, the present invention includes a medical device comprising a substrate that is expandable from a compressed state to an expanded state; a coating on the substrate and having a drug agent incorporated therein; and a sheath over the coating, the sheath being expandable from a compressed state to an expanded state and having at least one perforation therein. The medical device is configured such that when the substrate is in a compressed state, the sheath is likewise in a compressed state and the at least one perforation is substantially closed such that the drug agent does not pass through the at least one perforation. Moreover, when the substrate is in an expanded state, the sheath is likewise in an expanded state and the at least one perforation substantially opens such that the drug agent passes through the perforation.

In another aspect, the present invention includes a method for the localized delivery of drug agent to a target location within a mammalian body. The method comprises the steps of providing the medical device of the present invention; incorporating the drug agent into the coating of the device; delivering the medical device to the target location while the sheath is in a compressed state and the at least one perforation is substantially closed; and expanding the substrate to thereby expand the sheath such that the at least one perforation is substantially open. When the at least one perforation is substantially open, the drug agent moves from the coating through the perforation and into the body.

DETAILED DESCRIPTION

Figure 1:
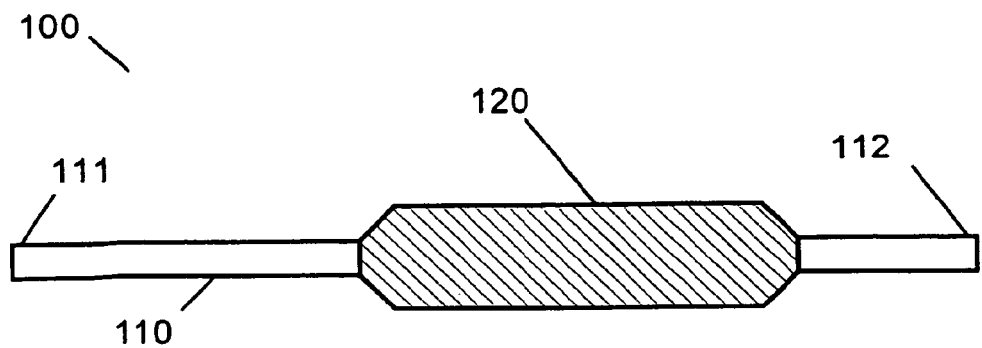
FIG. 1 shows an expandable catheter in accordance with an embodiment of the present invention.

The present invention provides medical devices and methods for the controlled, localized delivery of drug agents to target locations within a mammalian body while avoiding the premature release of drug agent during delivery. The medical devices of the present invention have a simple construction, provide a minimal cross-sectional profile, and allow for the easy and reproducible loading of drug agents.

The medical device of the present invention includes any one of a number of medical devices that are applicable to the localized delivery of drug agents within the body. When an expandable catheter is chosen as the medical device of the present invention, the expandable portion is preferably a balloon as described with specific reference to FIGS. 1-4. In this embodiment, the medical device 100 comprises an expandable catheter 110 having proximal and distal ends 111, 112. Mounted towards the distal end 112 of the catheter 110 is an expandable portion 120. The expandable portion 120 is a balloon, and more preferably, a perfusion balloon, as known in the art. Such balloon catheters are conventionally used for medical procedures such as, for example, angioplasty or the placement of stents to within body lumens such as coronary arteries.

The expandable portion 120 of catheter 110 is coated with a polymer for holding the drug agent during delivery into the body. The polymer coating 130 is preferably capable of absorbing a substantial amount of drug solution. The polymer coating 130 is placed onto the expandable portion 120 by any suitable mean such as, for example, immersing the expandable portion 120 into the polymer or a solution thereof, or spraying the polymer or solution thereof onto the expandable portion 120. The polymer is typically applied to a thickness of about 1 to 10 microns, preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto the expandable portion 120 of catheter 110. Such multiple layers can be of the same or different polymer materials.

The polymer coating 130 comprises any polymeric material capable of absorbing or otherwise holding the drug agent to be delivered. The polymeric material is, for example, hydrophilic or hydrophobic, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyacrylamides, polyethers, and copolymers thereof. Coatings from polymer dispersions such as polyurethane dispersions (BAYHYDROL, etc.) and acrylic latex dispersions are also within the scope of the present invention. The preferred polymer is polyacrylic acid, as described in U.S. Pat. No. 5,091,205, the disclosure of which is incorporated herein by reference. U.S. Pat. No. 5,091,205 describes medical devices coated with one or more polyisocyanates such that the devices become instantly lubricious when exposed to body fluids.

The medical device 100 includes an expandable sheath 210 (FIG. 2), which is sized to fit over the polymer-coated expandable portion 120 of the catheter 110. The sheath 210 comprises an elastic and resilient material such that it substantially conforms to the shape of the expandable portion 120 and expands and contracts with the expandable portion 120. In a preferred embodiment, the sheath 210 is biased towards a compressed state to hold the expandable portion 120 in a compressed state when it is not expanded, thus minimizing the profile of the medical device 100. Examples of materials used for the construction of the sheath 210 include metallic materials such as nitinol and stainless steel, and polymeric materials such as ethylene vinyl acetate, latexes, urethanes, polysiloxanes, styrene-ethylene/butylene-styrene block copolymers, silicone rubber, SILASTIC™, aliphatic polyesters, and mixtures and copolymers thereof.

Figure 2:
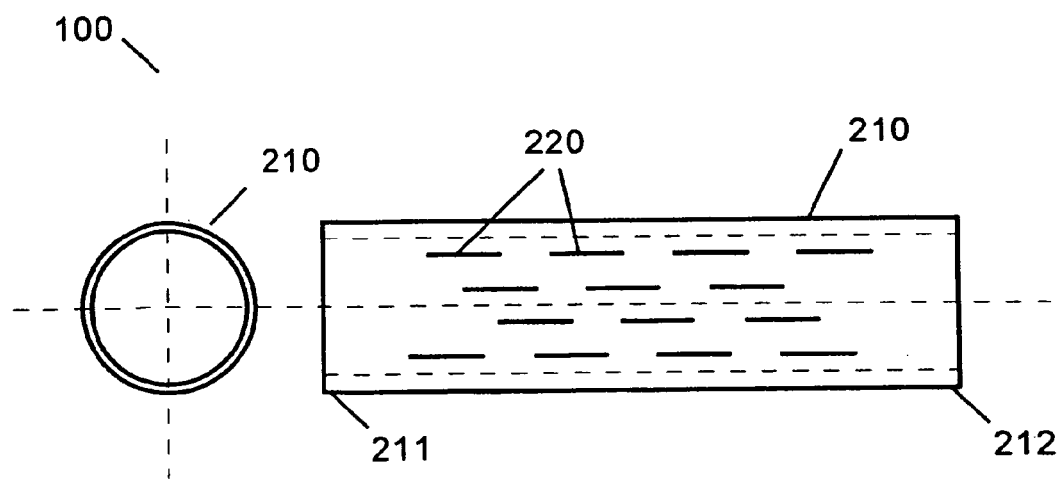
FIG. 2 shows side and end views of an expandable sheath in accordance with an embodiment of the present invention.
Figure 3:
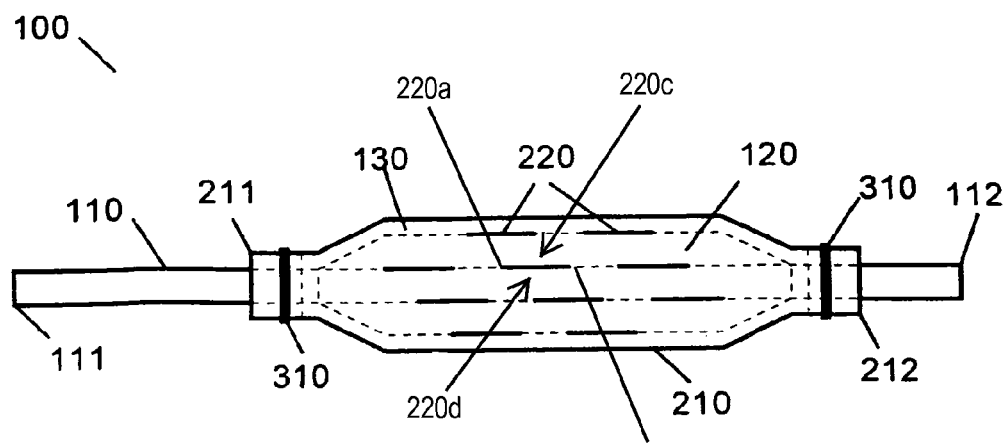
FIG. 3 shows an expandable catheter and overlying expandable sheath in a compressed state, in accordance with an embodiment of the present invention.

In the embodiment shown in FIG. 2, the sheath is a cylindrical tube having at least one perforation 220 therein. The sheath 210 is placed over the polymer-coated expandable portion 120 of the catheter 110 while in a deflated state as shown in FIG. 3. The proximal and distal ends 211, 212 of the sheath 210 are preferably attached to the catheter 110 such that the expandable portion 120 is completely covered by the sheath 210. The sheath 210 is attached to the catheter 110 by any suitable means, such as by adhesive materials and/or by winding a filament 310 (e.g., suture, etc.) around its proximal and distal ends 211, 212. The sheath 210 is of minimal thickness so to minimize the profile of the medical device 100. The preferred thickness of the sheath 210 is approximately 5 mils or less.

As shown in FIG. 3, the perforation(s) in the sheath 210 is (are) preferably longitudinal slits. As can be seen in FIG. 3, each slit is elongated and has a first end 220a, a second end 220b, a first side 220c, and a second side 220d. While it is within the scope of the invention for the sheath 210 to have a single perforation, it is preferred that the sheath 210 contain multiple perforations in the shape of longitudinal slits arranged in a staggered pattern. In one embodiment, the sheath 210 contains multiple longitudinally-oriented perforations which measure approximately 0.75 cm in length, and are spaced approximately 0.25 cm apart in a longitudinal direction and approximately 15.degree. apart in a radial direction.

The medical device 100 is delivered into the body while the expandable portion 120 is in a deflated shape as shown in FIG. 3. As such, the sheath 210 is in a compressed state and the perforations 220 are substantially closed such that the drug agent in the polymer coating 130 does not pass through the perforations 220. Delivery of the medical device 100 into the body and to a target location occurs, for example, through a body lumen (e.g., coronary arteries, portal vein, ileofemoral vein, etc.) by torquing or other known techniques.

Figure 4:
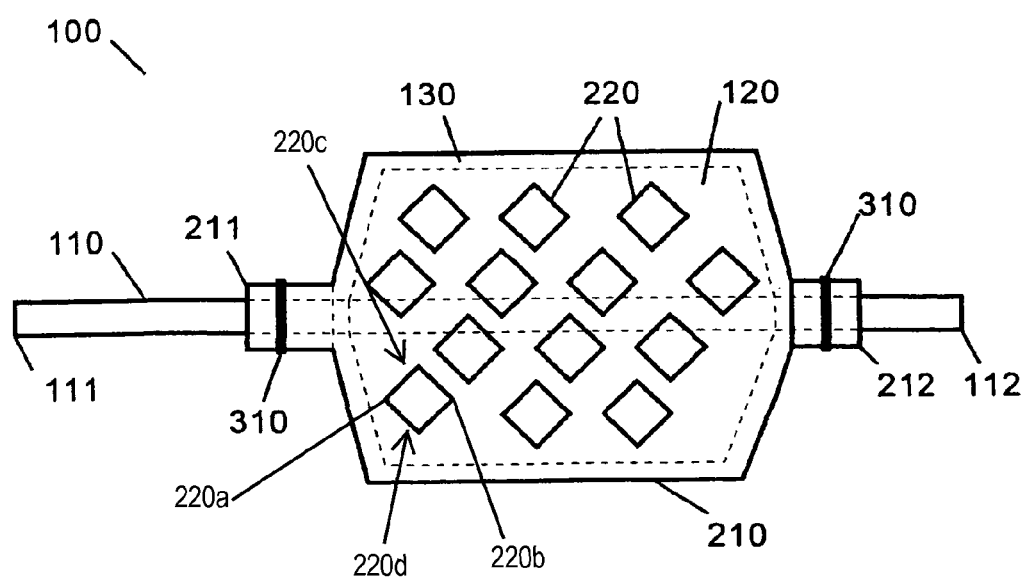
FIG. 4 shows an expandable catheter and overlying expandable sheath in an expanded state, in accordance with an embodiment of the present invention.

Once the medical device 100 is positioned to a target location within the body, the expandable portion 120 is expanded as shown in FIG. 4 to facilitate the release of drug agent from the polymer coating 130. The expandable sleeve 210 is constructed so that it will not rupture when the underlying expandable portion 120 of the catheter 110 is fully expanded. When the expandable portion 120 is in an expanded state, the sheath 210 is also in an expanded state and the perforations 220 become substantially open such that the drug agent in the polymer coating 130 passes through the perforations 220. As can be seen in FIG. 4, when the sheath 210 is expanded, each elongated slit opens such that first side 220c and second side 220d pull away from each other. The drug agent is released from the polymer coating 130 by any suitable mechanism, such as by diffusion or pressure-enhanced release.

The drug agents used in the present invention include, for example, pharmaceutically active compounds, proteins, oligonucleotides, genes, DNA compacting agents, gene/vector systems (i.e., anything that allows for the uptake and expression of nucleic acids), nucleic acids (including, for example, DNA, cDNA, RNA, antisense DNA or RNA), and viral, liposomes and cationic polymers that are selected from a number of types depending on the desired application. For example, biologically active solutes include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative-/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl ketone, a RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms. These and other compounds are added to the polymer coating using similar methods and routinely tested as set forth in the specification. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic polypeptides. A polypeptide is understood to be any translation product of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated into the polymer coating 130, or whose DNA can be incorporated, include without limitation, angiogenic factors including acidic and basic fibroblast growth factors, vascular endothelial growth factor, epidermal growth factor, transforming growth factor α and β, platelet-derived endothelial growth factor, platelet-derived growth factor, tumor necrosis factor .alpha., hepatocyte growth factor and insulin like growth factor; growth factors; cell cycle inhibitors including CD inhibitors; thymidine kinase ("TK") and other agents useful for interfering with cell proliferation, including agents for treating malignancies. Still other useful factors, which can be provided as polypeptides or as DNA encoding these polypeptides, include the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The drug agent is introduced into the polymer coating 130 by any suitable method. For example, the drug agent is placed in solution, which is thereafter applied to the polymer coating 130 by any suitable means, including dipping the polymer coating 130 into the drug solution or by applying the solution onto the coating 130 such as by pipet or spraying. In the former method, the amount of drug loading is controlled by regulating the time the polymer is immersed in the drug solution, the extent of polymer cross-linking, the concentration of the drug in the solution and/or the amount of polymer coating. In another embodiment of the invention, the drug is incorporated directly into the polymer prior to the application of the polymer as a coating onto a medical device. The drug agent can be applied to the polymer coating 130 either before or after the sheath 210 is placed over the coating 130. For example, if applied after the sheath 210 is placed over the coating 130, the expandable portion 120 is expanded to thereby open the perforations 220 in the sheath 210 as shown in FIG. 4. The drug agent is thereafter incorporated into the polymer coating 130 through the open perforations 220 by any suitable means such as, for example, dipping the medical device 100 into a solution of drug agent. The method of incorporating the drug agent into the coating 130 through the open perforations 220 is generally preferred, especially where the polymer coating 130 is loaded multiple times with the same or different drug agents.

The release profile of the drug from the polymer coating 130 is determined by many factors including the drug solubility, the thickness and porosity of the polymer coating, and the number and size of perforations 220 in the sheath 210. When an expandable member such as a balloon catheter is used to administer the drug, pressure can be used to increase the rate of drug transfer to the tissue. An increase in pressure increases the diameter of the balloon and therefore the diameter of the surrounding tissue (if contacted by the balloon), thereby increasing the surface area for drug transfer. The amount of drug that is delivered per unit time is therefore increased. An increase in the rate of drug release from the polymer coating 130 is also accomplished by increasing both the number and size of perforations 220 in the sheath 210.

During drug administration, a substantial amount of the drug agent contained in the polymer coating 130 is diffused into the affected area. The inflation pressure needed to expand the expandable portion 120 of catheter 110 is typically in the range of about 1 to 20 atm. When the expandable portion 120 comprises a balloon, it is formed of any suitable material such as vinyl polymers such as polyethylene; polyesters such as polyethylene terephthalate; polyamides such as nylon; polyolefins and copolymers thereof (e.g., Selar, Pebax, Surlyn, Hytrel, etc.). The balloon is optionally a perfusion balloon, which allows blood to perfuse the catheter to prevent ischemia during delivery. A perfusion balloon is particularly preferred for long arterial delivery times and when the delivery drug is only very slightly soluble in water.

Figure 5:
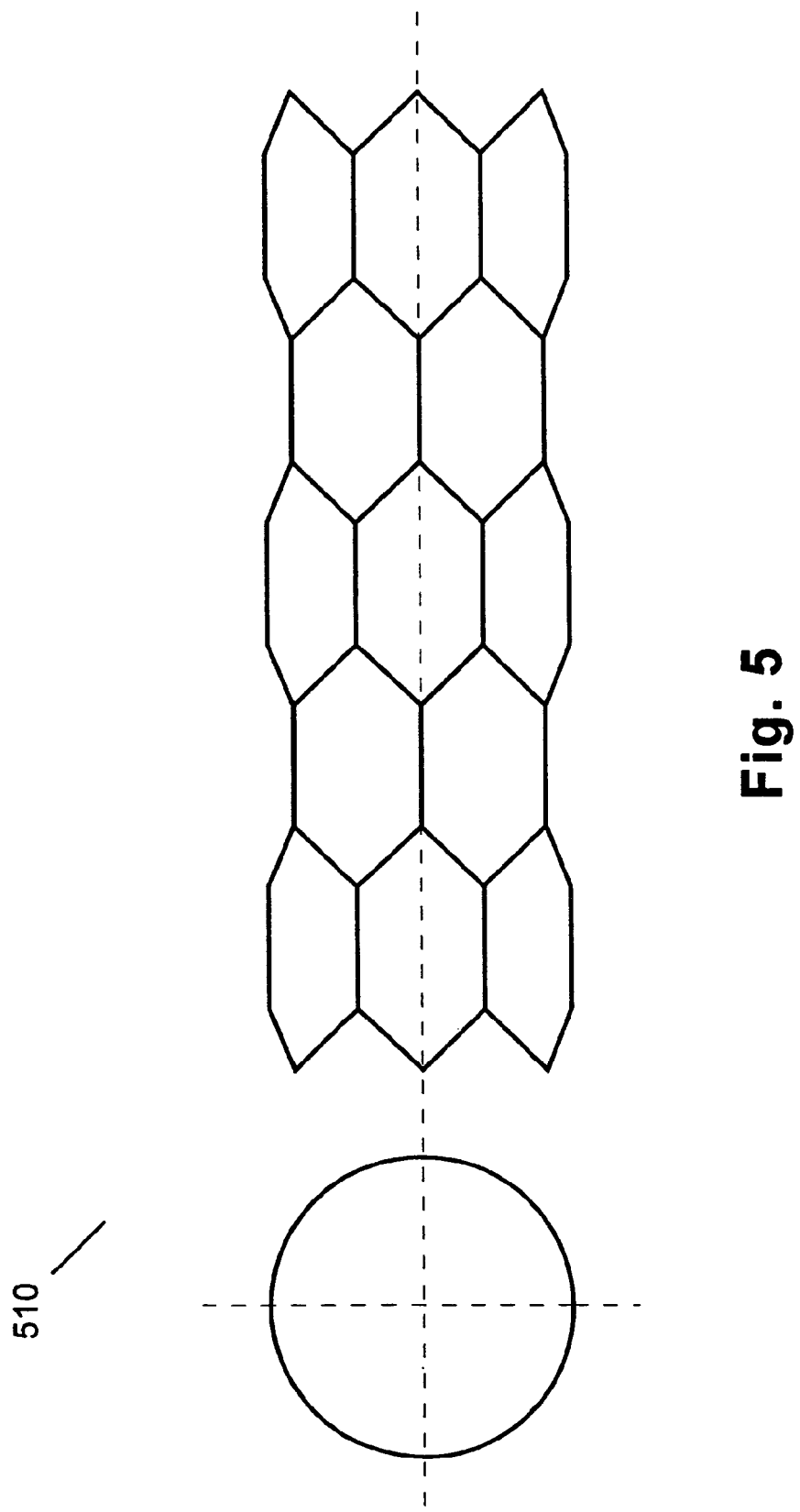
FIG. 5 shows side and end views of a stent used in an embodiment of the present invention.

In one embodiment, the medical device 100 of the present invention includes a stent 510 (FIG. 5) for placement in a body lumen. The present invention can thus be used for the dual purpose of localized drug delivery and stent placement. As known in the art, stents are tubular support structures that are implanted inside tubular organs, blood vessels or other tubular body lumens. The stent used with the present invention is of any suitable design, and is either self-expanding or balloon-expandable. The stent is made of any suitable metallic (e.g., stainless steel, nitinol, tantalum, etc.), polymeric (e.g., polyethylene terephthalate, polyacetal, polylactic acid, polyethylene oxide-polybutylene terephthalate copolymer, etc.) or biodegradable material. The stent 510 is preferably metallic and configured in a mesh design, as shown in FIG. 5. When used with the present invention, the stent 510 is placed over the sheath 210 when each of the expandable portion 120, the sheath 210, and the stent 510 are in a compressed state. The medical device 100 is thereafter delivered to a target location within the body, as previously described. In this embodiment, the target location is situated within a body lumen. When the expandable portion 120 is expanded to release the drug agent from the polymer coating 130, the stent 510 is likewise expanded. After the drug agent has been released from the polymer coating 130, the expandable portion 120 is compressed or deflated such that the sheath 210 is compressed with the expandable portion 120. The stent 510, however, remains in its expanded state within the body lumen.

The medical device of the present invention is optionally used to accomplish electroporation, in which short pulses of high electric fields are applied to a target location in the body to thereby cause cell membranes to become porous so that drug agents can diffuse therein. Any suitable modification of the medical device is made to facilitate electroporation as is known in the art, such as, for example, the inclusion of electrodes. The medical device of the present invention may also be modified, as is known in the art, for accomplishing iontophoresis in which a current is applied at the target location to promote the delivery of ionic drug agents.

The present invention provides a system and method for the localized delivery of drug agent to target locations within a mammalian body. Although the present invention has been described with respect to several exemplary embodiments, there are many other variations of the above-described embodiments which will be apparent to those skilled in the art, even where elements have not explicitly been designated as exemplary. It is understood that these modifications are within the teaching of the present invention, which is to be limited only by the claims appended hereto.

What is claimed is:

1. A medical device, comprising:
    a balloon that is expandable from an unexpanded state to an expanded state;
    an elastic sheath over said balloon, said elastic sheath being expandable from an unexpanded state to an expanded state and having at least one slit therein, said slit having a first side and a second side, wherein said first side and said second side are substantially closed in the unexpanded state, and said first side and said second side pull away from each other in the expanded state; and
    a drug agent carried by the medical device such that when said at least one slit is substantially closed, said drug agent is substantially retained by the elastic sheath,
    wherein when said balloon is in the unexpanded state, said elastic sheath is in the unexpanded state, and when said balloon is expanded to the expanded state, said elastic sheath is expanded to the expanded state and said at least one slit is substantially open such that said drug agent is delivered from said medical device.

2. The medical device of claim 1, wherein the medical device further comprises a polymer for carrying the drug agent, the polymer selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyacrylamides, polyethers, polyurethane dispersions, acrylic latex dispersions, and mixtures and copolymers thereof.

3. The medical device of claim 1, wherein said drug agent comprises a drug agent selected from the group consisting of pharmaceutically active compounds, proteins, oligonucleotides, DNA compacting agents, recombinant nucleic acids, gene/vector systems, and nucleic acids.

4. The medical device of claim 1, wherein said elastic sheath comprises a material selected from the group consisting of ethylene vinyl acetate, latexes, urethanes, polysiloxanes, styrene-ethylene/butylene-styrene block copolymers, aliphatic polyesters, and mixtures and copolymers thereof.

5. The medical device of claim 1, wherein said drug agent comprises paclitaxel.

6. The medical device of claim 1, wherein said at least one slit comprises a plurality of slits arranged in a staggered pattern.

7. The medical device of claim 1, wherein said balloon comprises at least part of a portion of a balloon catheter.

8. The medical device of claim 7, wherein said elastic sheath is tubular and surrounds said balloon portion of said balloon catheter.

9. The medical device of claim 1, wherein said balloon is not configured to receive a drug agent therethrough.

10. The medical device of claim 1, further comprising a stent over the elastic sheath.

11. A method for the localized delivery of a drug agent to a target location within a mammalian body, comprising the steps of:
    using a medical device comprising:
        a balloon that is expandable from an unexpanded state to an expanded state;
        an elastic sheath over said balloon, said elastic sheath being expandable from an unexpanded state to an expanded state and having at least one slit therein, said slit having a first side and a second side, wherein said first side and said second side are substantially closed in the unexpanded state, and said first side and said second side pull away from each other in the expanded state; and
        a drug agent carried by the medical device such that when said at least one slit is substantially closed, said drug agent is substantially retained by the elastic sheath,
        wherein when said balloon is in the unexpanded state, said elastic sheath is in the unexpanded state, and when said balloon is expanded to the expanded state, said elastic sheath is expanded to the expanded state and said at least one slit is substantially open such that said drug agent is delivered from said medical device;
    delivering said medical device to said target location while said elastic sheath is in the unexpanded state and said at least one slit is substantially closed; and
    expanding said balloon to thereby expand said elastic sheath to the expanded state such that said at least one slit is substantially open, whereby the drug agent is delivered from said medical device.

12. The method of claim 11, wherein said drug agent is incorporated into said medical device by the steps of:
    expanding said balloon to thereby expand said elastic sheath such that said at least one slit is substantially open;
    exposing said drug agent to said medical device while said at least one slit is substantially open; and
    deflating said balloon to thereby return said elastic sheath to the unexpanded state such that said at least one slit is substantially closed.

13. The method of claim 11, wherein said drug agent is selected from the group consisting of pharmaceutically active compounds, proteins, oligonucleotides, genes, DNA compacting agents, gene/vector systems, and nucleic acids.

14. The method of claim 11, wherein said elastic sheath comprises a material selected from the group consisting of ethylene vinyl acetate, latexes, urethanes, polysiloxanes, styrene-ethylene/butylene-styrene block copolymers, aliphatic polyesters, and mixtures and copolymers thereof.

15. The method of claim 11, wherein said at least one slit comprises a plurality of slits arranged in a staggered pattern.

16. The method of claim 11, wherein said balloon comprises at least part of a portion of a balloon catheter.

17. The method of claim 16, wherein said elastic sheath is tubular and surrounds said balloon portion of said balloon catheter, said tubular elastic sheath having proximal and distal ends.

18. The method of claim 17, wherein said proximal and distal ends of said elastic sheath are attached to said balloon catheter such that said balloon portion is completely covered by said elastic sheath.

19. The method of claim 11, wherein said medical device comprises an iontophoresis catheter or an electroporation catheter.

20. The method of claim 11, further comprising a stent over the elastic sheath.

* * * * *